United States Patent [19]
Tsujikawa

[11] Patent Number: 5,304,153
[45] Date of Patent: Apr. 19, 1994

[54] APPARATUS AND SYSTEM FOR THE SELF-DOSING OF A LIQUID MEDICINE

[75] Inventor: Hajime Tsujikawa, Osaka, Japan

[73] Assignee: Nissho Corporation, Osaka, Japan

[21] Appl. No.: 910,886

[22] Filed: Jul. 10, 1992

[30] Foreign Application Priority Data

Jul. 10, 1991 [JP] Japan .................................. 3-195709

[51] Int. Cl.⁵ .............................................. A61M 5/00
[52] U.S. Cl. .................................. 604/132; 604/93
[58] Field of Search ............... 604/132, 133, 134, 135, 604/131, 185, 9, 10, 93

[56] References Cited

U.S. PATENT DOCUMENTS

| | | | |
|---|---|---|---|
| 3,048,171 | 8/1962 | Grau | 604/134 |
| 4,560,375 | 12/1985 | Schulte et al. | 604/9 |
| 4,968,301 | 11/1990 | di Palma et al. | 604/132 |
| 4,978,338 | 12/1990 | Melsky et al. | 604/93 |
| 5,061,243 | 10/1991 | Winchell et al. | 604/132 |

FOREIGN PATENT DOCUMENTS

| | | |
|---|---|---|
| 483759 | 5/1992 | European Pat. Off. |
| 2588757 | 4/1987 | France |
| 63-501195 | 5/1988 | Japan |
| WO90/12609 | 11/1990 | PCT Int'l Appl. |
| 2192135 | 1/1988 | United Kingdom |

*Primary Examiner*—John D. Yasko
*Attorney, Agent, or Firm*—Armstrong, Westerman, Hattori, McLeland & Naughton

[57] ABSTRACT

An apparatus for the self-dosing of a liquid medicine. The apparatus includes a chamber formed in a casing for receiving a liquid medicine to be self-dosed by a patient, with an inlet and outlet port formed to communicate with the chamber free from leakage of the medicine. The apparatus further includes a piston fitted liquid-tightly in the chamber, a push button attached to and adapted to actuate the piston and which is capable of being pressed by the patient a desired number of times corresponding to an amount of liquid medicine to be dosed, and a spring urging the piston towards its home position. After the patient presses the button and removes his hand from the button, the spring forces the piston backwards to its home position and the resulting negative pressure causes a subsequent smooth refilling of the chamber. The apparatus, which is a simple structure and can be manufactured at a low cost, can be employed in an integrated system for the self-dosing of the liquid medicine.

2 Claims, 3 Drawing Sheets

APPARATUS AND SYSTEM FOR THE SELF-DOSING OF A LIQUID MEDICINE

BACKGROUND OF THE INVENTION

1. Field of the Invention

The present invention relates to an apparatus for the self-dosing of a liquid medicine and also to a system in which the apparatus is incorporated. More particularly, the present invention relates to an apparatus which may be incorporated in a system or used as an independent device so as to be operated by a patient for the purpose of repeatedly dosing small amounts of, for example, analgesics to relieve postoperative pain or small amounts of an anticancer medicine to relieve cancer pain, or one-shot dosing of other medicines.

2. Description of the Related Art

It is becoming popular in anesthetic treatment to repeat or continue the administration of small amounts of an analgesic for the control of postoperative or cancer pain, wherein a certain device is used and an epidural catheter is inserted into a patient's body. On the other hand, the conditions of patients vary, and some patients may suffer acute pain during the continuous administration of prescribed amounts of analgesics. Therefore, there have been proposed various kinds of apparatuses adapted for use by a patient himself or herself in the event of such acute pain. These apparatuses are designed to allow the patient to make a one-shot administration of an analgesic, as disclosed for example in Domestic Republishing Gazette Sho. 63-501195 of an International Patent Application.

This apparatus for the patient-controlled delivery of a beneficial agent comprises, as shown in FIG. 5(a) of the present application, a chamber 90 defined between a raised plateau 98 of a back plate 86 and a circular flexible sheet 96. The chamber 90 is connected to conduits, which are respectively attached to and communicate with a bladder or container of the agent and to a catheter or other medical device. The flexible sheet 96 supports a floating plate 100 disposed thereon. A button-like control switch 84 is located above the floating plate so as to be pushed thereto by the patient. A base portion of the control switch 84 is journaled on the back plate by a pivot pin 116, and a coil spring 124 surrounds this pin. When the switch 86 is pushed by the patient, the chamber 90 will be compressed as shown in FIGS. 5(b) and 5(c) so that the beneficial agent is supplied to him or her via one of the conduits. Upon retraction of the patient's finger from the button-like switch 84, the coil spring 124 causes it to return to its home position shown in FIG. 5(d).

It is noted here that the flexible sheet 96 in the prior art apparatus remains pressed as illustrated in FIG. 5(d), even after the patient has removed his or her finger from the switch 84. Thus, the refilling of the chamber 90 with the beneficial agent is done only by a moderate compressive force imparted by the bladder to the beneficial agent therein. The elastomeric bladder is, however, of such a nature that only small amounts of the agent can be dosed. Consequently, the beneficial agent is fed to the chamber at a slow speed (see Gazette 63-501195, page 6, lines 13-19).

This feature of the prior art apparatus is disadvantageous in that prompt and rapid refilling of the agent for the next dose is not possible.

Further, the patient cannot change or adjust the quantity of one dose, because only a limited volume of the agent can be discharged at a time by means of the conventional apparatus. Such a limited quantity and a slow refilling render it impossible for the patient to dose himself or herself a freely selected quantity of the agent at any desired rate.

It is also noted that, as can be seen in FIGS. 5(a) to 5(d), this conventional apparatus is of a comparatively complicated structure which can be manufactured only at a relatively high cost. In addition, the liquid agent is likely to leak from the periphery of the flexible sheet 96.

SUMMARY OF THE INVENTION

Therefore, an object of the present invention is to provide an apparatus which is adapted for the self-dosing of a liquid medicine, is capable of being refilled rapidly with the agent and of adjusting the quantity of the agent to be dosed at a time, and further is free from leakage of the agent, though it is of a comparatively simple structure and can be manufactured at a reduced cost. Another object of the invention is to provide a system in which such an apparatus is incorporated as one of principal elements.

In order to achieve the above objects, the apparatus according to the present invention comprises a device which consists of a casing formed with a chamber for receiving a liquid medicine and with inlet and outlet ports in fluid communication with the chamber, a piston liquid-tightly and slidably fitted in the chamber, a push button attached to the piston and capable of being pressed manually by a patient, and a spring urging the piston backwards to its home position.

In a preferred embodiment, the apparatus of the invention further comprises upstream and downstream conduits respectively connected to the inlet and outlet ports for transportation of the liquid medicine, and a check valve disposed in the downstream conduit at its end so that only a forward flow of the liquid medicine is allowed, whereby a backward flow thereof is inhibited.

The present invention provides also a system for the self-dosing of a liquid medicine, the system including, in combination with the preferred embodiment of the apparatus, a continuous feeder "D" having a usual dosing line through which the liquid medicine continuously flows at a low flow rate, the dosing line being connected to the apparatus in parallel and in fluid communication therewith.

Alternatively, the system may include, in combination with the preferred embodiment of the apparatus, a medicine bag connected in series to the apparatus by a thin external tube having an extremely small inner diameter, through which tube the liquid medicine is fed to the apparatus.

In operation, the push button in the apparatus is pressed by a patient in order to force the piston towards the bottom of the chamber, so that the liquid medicine flows out of the chamber through the output port, until the patient removes his or her finger(s) from the push button. Simultaneously with the retraction of the button, the spring elastically forces the piston towards its unactuated home position, whereby the chamber will be refilled with the liquid medicine which is automatically sucked into the chamber due to a negative pressure produced in said chamber. The refilling of the chamber is effected in a short time in this manner. Therefore, a second and succeeding dose(s) can be administered by the apparatus or the system employing the same of the invention, without any significant delay. Thus, an amount of administered medicine can be chosen easily by relying on the number of repeated doses.

Because the device in the apparatus provided herein for the self-dosing of liquid medicine is composed of only four main parts, that is, the casing, the piston, the push button and the spring, its structure is so simple that it can be manufactured at a reduced cost. It is another important feature that the piston is made of a gasket material which is highly reliable in its sealing property, avoiding the problem of leakage of the medicine.

BRIEF DESCRIPTION OF THE DRAWINGS

In the accompanying drawings showing embodiments of the present invention.

DETAILED DESCRIPTION OF THE PREFERRED EMBODIMENT

Figure 1:
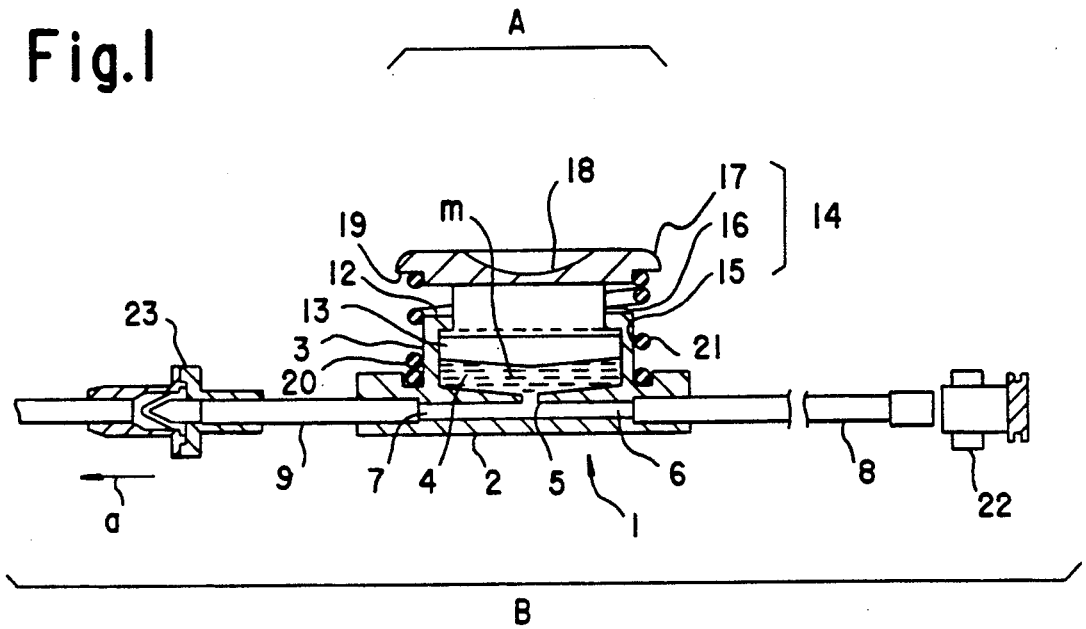
FIG. 1 is a cross-sectional view of an apparatus for the self-dosing of liquid medicine of a first embodiment.
Figure 2:
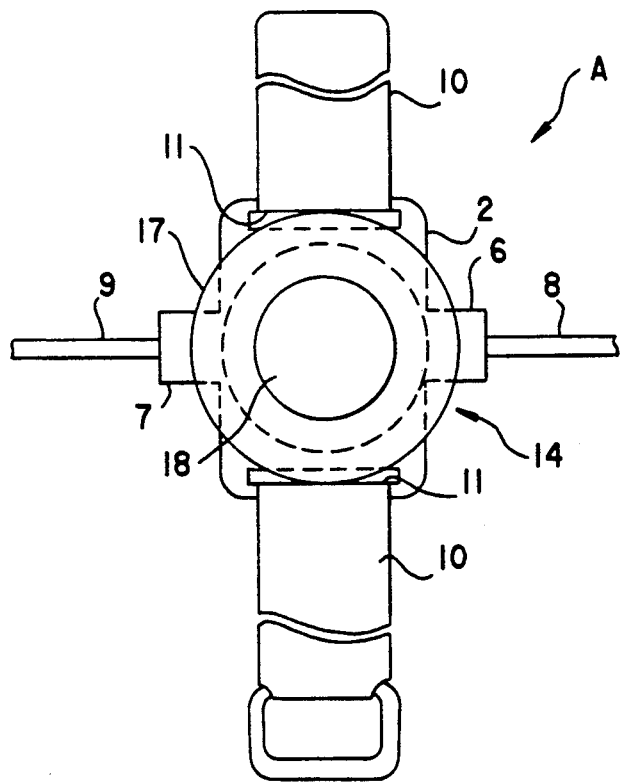
FIG. 2 is a plan view of the apparatus.

As shown in FIG. 1 which is a cross-sectional view of an apparatus provided according to the present invention, and shown in FIG. 2 which is a plan view of a device "A" included in the apparatus, the apparatus comprises a casing 1 composed of a base portion 2 and a cylindrical portion 3 integral therewith. The interior of the cylindrical portion 3 is formed as a chamber 4 in which a liquid medicine "m" is received. An aperture 5 opens through a bottom of the chamber 4 to the junction of inlet and outlet ports 6 and 7 which are members of the apparatus and penetrate the base portion 2. Alternatively, the inlet and outlet ports 6 and 7 may be separated insofar as they are in fluid communication with the chamber 4. Secured to the top of cylindrical portion 3 is a stopper 12 for holding a piston 13 in the chamber, the piston being made of a gasket material such as described below. The casing may be made of a transparent plastic, for example, ABS resin.

The casing 1 is substantially of a size of a man's wrist watch, and may have slits 11 for fixing the ends of a pair of bands 10 and 10 so that the apparatus can be worn by a patient on his or her wrist. It is desirable that the periphery of casing 1 is graduated with a scale, for example 1 ml, 2 ml, 3 ml and so on, proportional to the number of times of pressing the push button 14.

The piston 13 liquid-tightly fits in the cylindrical portion 3 of the casing 1. The push button 14 is attached to the piston 13, which is made of an elastic rubber such as a butyl rubber so that a sufficient sealing property is imparted to the piston. The push button 14 comprises integral portions, that is, a disc 15 carrying the piston attached thereto, a rod 16 extending from the disc, and a head 17 formed at the top of rod 16. A recess 18 formed on the upper central surface of the head is provided for easy pressing thereof by the patient. This push button 14 is made of a plastic such as polypropylene.

An annular seat 19 formed on the periphery of the lower surface of the head 17 faces another annular seat 20 on the outer periphery around the bottom of the cylindrical portion 3 of the casing 1. A coil spring 21 is held in place between the seats 19 and 20. This spring urges the push button 14 upwardly in FIG. 1 so that the button takes its uppermost position within the chamber 4 unless it is pressed by the patient.

If and when the patient presses the push button 14, the liquid medicine "m" will be compressed and discharged at the same time out of said chamber 4 through the output port 7. Upon removal of the patient's finger from the button 14, the piston returns promptly to its uppermost position, thereby producing a negative pressure in the chamber 4 and refilling it with the liquid medicine sucked through the inlet port 6. The chamber 4 is refilled again in this manner simultaneously with the return of button 14 to its home position.

Since instantaneous refilling of the chamber in the apparatus with the liquid medicine "m" is effected every time the push button 14 is pressed, a desired amount of the medicine can be supplied to the patient by the repeated pressing of the button. Only four parts, i.e., the casing 1, push button 14, piston 13 and spring 21, constitute the device, or reservoir, "A" as the principal member of the apparatus. Such a simplified structure of the device, or reservoir, enables manufacture thereof at a reduced cost. The sealing of chamber 4, which is realized by close contact of the inner periphery of the cylindrical portion 3 with the outer periphery of piston 13, is highly reliable because the piston is made of a gasket material which elastically and tightly engages with said inner periphery. Thus, there is no possibility of leakage of the medicine in the apparatus.

An upstream conduit 8 may be connected to the inlet port 6 of the apparatus as described above, with a downstream conduit 9 being connected to the outlet port 7. A "Luer-tapered" line connector 22 and a check valve 23 are connected to ends of the upstream and downstream conduits 8 and 9, respectively. The check valve 23 allows the medicine only to flow forward in the direction indicated by the arrow "a", and inhibits it from flowing in a reverse direction.

The apparatus "B" for the self-dosing of liquid medicine is constructed in the manner described above, and particularly includes the check valve 23 so that the liquid medicine is sucked into the chamber only through the upstream conduit 8. By virtue of the line connector 22 and check valve 23, this apparatus "B" can be connected readily to a usual dosing line in a continuous dosing system or the like, without detaching said apparatus from the patient's arm or wrist.

Next, a system "C" for the self-dosing of liquid medicine will be described below, which system is provided in a further embodiment and in which system the apparatus "B" is employed.

Figure 3:
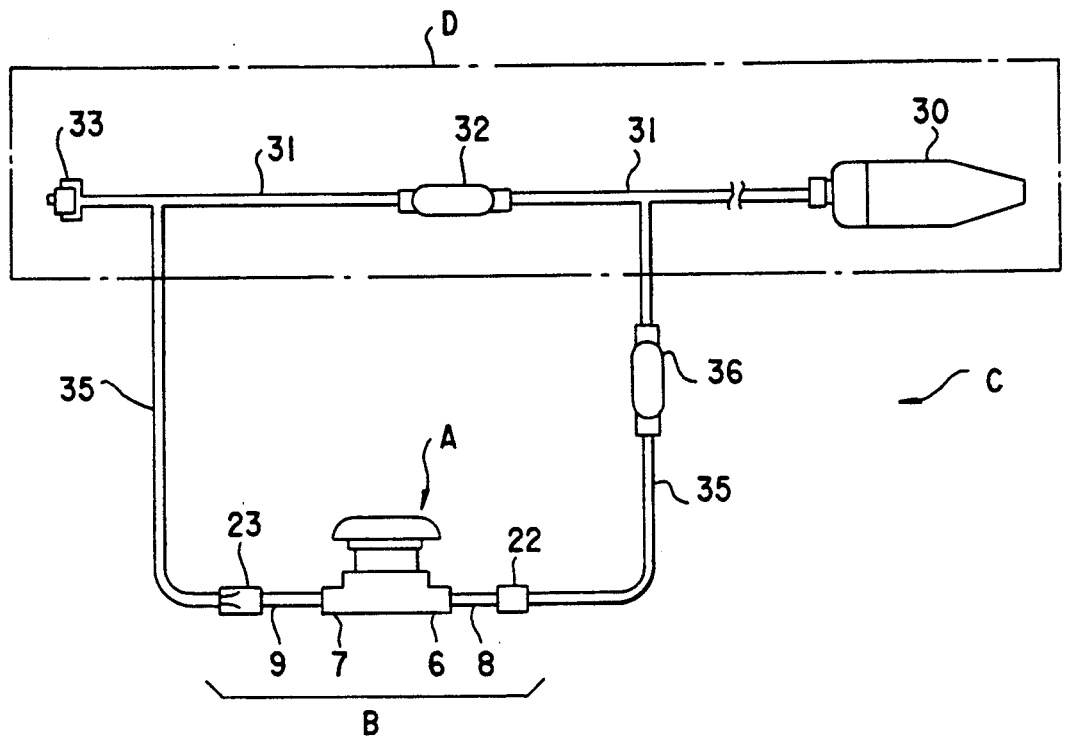
FIG. 3 is a schematic view of a system for the self-dosing of liquid medicine of a second embodiment.

As shown in FIG. 3, this system "C" comprises a continuous feeder "D" combined with the apparatus "B" and having a usual dosing line through which the liquid medicine continuously flows at a low flow rate. The feeder "D" is composed of: a medicine receptacle 30 having a dosing pump; a dosing tube 31 extending from the receptacle; and a flow control means 32 disposed along this tube between the pump and a terminal connector 33 attached to a free end of the tube 31. The connector 33 may be joined to a catheter or the like so that the medicine pumped out of the receptacle 30 is dosed to a patient at an extremely low flow rate, for example at 1 ml/Hr, which flow rate is controlled by the control means 32.

In addition to the usual dosing line composed of the dosing tube 31 in this system, a bypass line is provided which comprises external tubes 35 and 35. One end of each of tubes 35 is connected to the usual dosing line, and the other end of each of said tubes 35 is connected to the apparatus "B". Another flow control means 36 is also disposed on one of the external tubes 35, whereby the flow of medicine into the device or reservoir "A" is limited to, for example, 1 ml/Hr.

In the operation of such a system "C", the liquid medicine flowing out of the receptacle 30 diverges into the dosing tube 31 and external tube 35, wherein a fraction of the medicine travels through the control means 32 in the usual dosing line so as to be directly dosed to the patient to whom this system is applied. Another fraction flows through the bypass and advances beyond the other control means 36, so as to be received temporarily in the device "A" before being dosed to the patient through the check valve 23. Thus, under a normal condition in this example, a total dose of 2 ml/Hr is given to the patient. However, if and when this patient suffers acute pain, he or she may press the push button 14 to one-shot dose himself or herself instantaneously with the medicine present in the reservoir "A".

Although an example of a flow rate which is controlled respectively by the control means 32 and 36 is 1 ml/Hr, it may be changed within a range of 0.5-2.5 ml/Hr, taking into account the symptoms of a patient and/or the concentration, i.e., dilution ratio, of the liquid medicine. Since the volume of reservoir "A" is 2-3 ml in this example, the one-shot dose may be about 2.5-5.5 ml in volume. A dose during the refilling of reservoir "A" after the emergency one-shot dose will be continued only through the usual dosing line at a flow rate controlled by the means 32 disposed along this line.

Figure 4:
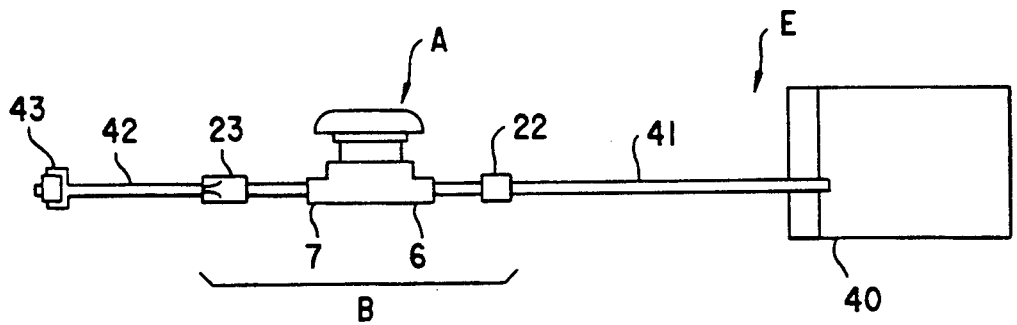
FIG. 4 is a schematic view of another system for the self-dosing of liquid medicine of a third embodiment.
Figure 5A:
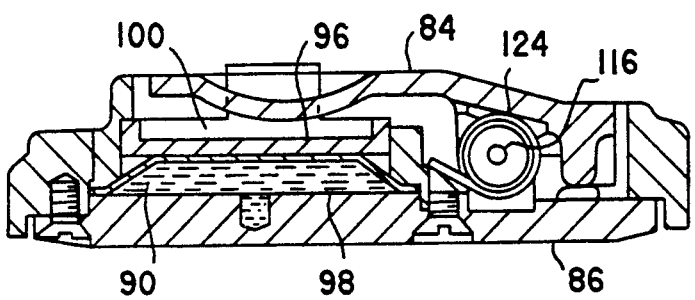
FIGS. 5(a) to 5(d) illustrate a prior art apparatus for the self-dosing of liquid medicine.
Figure 5B:
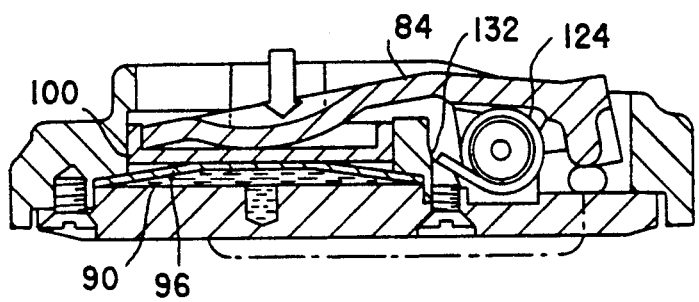
Figure 5C:
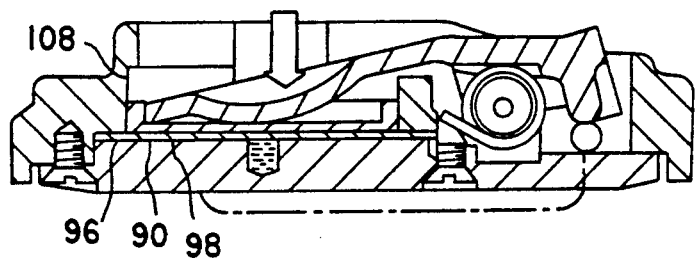
Figure 5D:
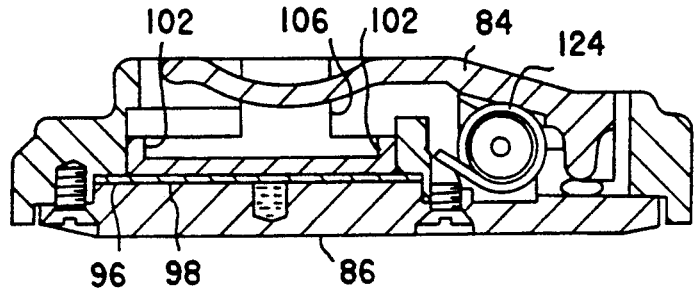

FIG. 4 illustrates a further embodiment wherein another system "E" is designed only for one-shot doses.

A medicine bag 40 in this embodiment can usually have a capacity of 20-100 ml, or, more preferably, 40-60 ml. A thin external tube 41, which connects the medicine bag 40 to the reservoir "A", is of a very small inner diameter, for example, 50-200 μm. Since such a thin tube 41 per se regulates the flow rate of the liquid medicine, a flow control means is dispensed with, thus rendering simpler the structure of this system. Another external tube 42 having a terminal connector 43 is connected to the outlet of the device or reservoir "A" so that the reservoir can be adjoined to a catheter or other medical device.

In operation, the push button 14 is pressed and subsequently not pressed so that reservoir "A" automatically sucks an amount of liquid medicine from the bag 40.

With the system being initially set in this state, the patient can press the button to dose himself or herself with the analgesic whenever he or she suffers pain. Thus, this system is adapted in particular for the instantaneous one-shot dosing of the liquid medicine.

The time needed to refill the chamber or reservoir with the medicine will depend on the inner diameter and length of the thin external tube 41, and will also depend on the reservoir capacity and the magnitude of negative pressure produced therein. A refilling time of from 30 minutes to 1 hour is desirable from a practical point of view.

It will now be apparent that the apparatus provided by the present invention for the self-dosing of liquid medicine is advantageous not only in that the refilling time is relatively short, and the amount of doses can be selected freely, but also in that there is no possibility that the liquid medicine will leak out of the apparatus in spite of the simple structure which can be manufactured at a reduced cost.

Further, the apparatus is useful either to cooperate with a slow continuous dosing system, or with a system which is specified only to effect the one-shot self-dosing of liquid medicine.

What is claimed is:

1. An apparatus for the self-dosing of a liquid medicine, comprising:
    a casing formed with a chamber for receiving the liquid medicine and with an inlet port and an outlet port in fluid communication with the chamber,
    a piston liquid-tightly and slidably fitted in the chamber,
    a push button attached to the piston and capable of being pressed by a patient using the apparatus to move the piston from a home position to a pressed position, a one-way check valve communicating with said outlet port and
    a spring which cooperates with the push button and urges the piston towards its home position to enable rapid refilling of the chamber with fresh liquid medicine, wherein said check valve allows only a forward flow and inhibits a backward flow of the liquid medicine.

2. An apparatus as defined in claim 1, further comprising upstream and downstream conduits for transporting the liquid medicine, the conduits being connected to said inlet and outlet ports, respectively, and wherein said check valve is disposed in the downstream conduit at its end.

* * * * *